United States Patent [19]

Wong et al.

[11] Patent Number: 5,239,091

[45] Date of Patent: Aug. 24, 1993

[54] 2-DEOXY DERIVATIVES OF N-ACETYL NEURAMINIC ACID AND THEIR PREPARATION

[75] Inventors: Chi-Huey Wong, College Station; William J. Hennen, Bryan, both of Tex.

[73] Assignee: G. D. Searle & Co., Chicago, Ill.

[21] Appl. No.: 789,227

[22] Filed: Nov. 7, 1991

Related U.S. Application Data

[60] Division of Ser. No. 711,559, May 30, 1991, abandoned, which is a continuation of Ser. No. 238,357, Aug. 30, 1988, abandoned.

[51] Int. Cl.$^5$ .............................. C07D 309/10
[52] U.S. Cl. ................... 549/419; 549/417
[58] Field of Search ................. 549/419, 417

[56] References Cited

U.S. PATENT DOCUMENTS 4,730,058 3/1988 Ogawa et al. .................. 549/214

FOREIGN PATENT DOCUMENTS 61-243074 10/1986 Japan .

OTHER PUBLICATIONS

Luthman et al. Synthesis of C-Glycosides of etc. J. Org. Chem., 52, 3777–84 (1987).
Baggett et al. Reinvestigation of the Synthesis of etc. Carb. Res., 110, 11–18 (1982).
Auge et al. Synthesis With An Immobilized Enzyme of etc. Tet. Lett., 26(20), 2439–2440 (1985).
Auge et al. Synthesis with Imobilized Enzyme of the Most etc. Tet. Lett., 25(41), 4663–64 (1984).
Auge et al. The Use of an Immobilized Aldolase in the etc. JCS. Chem. Comm., 859–860 (1987).
Meindl et al. 2–Deoxy-2,3–dehydrosialic acids. II. etc. Chem. Abstr., 71:109318b (1969).
Kim et al. Enzymes in Carbohydrate Synthesis: etc. Chem. Abstr., 109:125381a (1988).

*Primary Examiner*—Nicky Chan
*Attorney, Agent, or Firm*—Cynthia S. Kovacevic; Roger A. Williams; Paul D. Matukaitis

[57] ABSTRACT

The present invention relates to 2-deoxy-N-acetyl-neuraminic acid derivatives and methods for their preparation.

12 Claims, 1 Drawing Sheet

2-DEOXY DERIVATIVES OF N-ACETYL NEURAMINIC ACID AND THEIR PREPARATION

This is a division, of application Ser. No. 07/711,599, filed May 30, 1991, now abandoned, which is a continuation of application Ser. No. 07/238,357, filed Aug. 30, 1988, now abandoned.

BACKGROUND OF THE INVENTION

The present invention relates to 2-deoxy derivatives of N-acetylneuraminic acid and to methods of their preparation.

Sialic acids, nonulosaminic acids, are a family of amino sugars that are derivatives of N-acetylneuraminic acid (Neu5Ac). Sialic acids are widely distributed through the animal kingdom and play many important roles in molecular recognition. Schauer, R. *Adv. Carbohydr. Chem. Biochem.* 40 (1982) 131. Schauser, R., "Sialic Acids," Springer-Verlag: Wein and New York, 1982. Howe, C., Lee, L. T. *Adv. Virus Res.* 17 (1982) 1. Also, certain types of cancer cells have been shown to contain higher levels of sialic acids than the corresponding normal cells. Van Boeckel, C. A. A. *Recl. Trav. Chim. Pays-Bas* 105 (1986) 35. Yogees Waren, G., Salk, P. C. *Science* (Washington, D.C.) 212 (1981) 1514.

Neu5Ac derivatives are useful as glycosyl donors for the enzymatic syntheses of oligosaccharides present in glycoproteins and glycolipids via CMP-Neu5Ac. David, S., Auge, C. *Pure Appl. Chem.* 59 (1987) 1501. Higa, H. H., Paulson, J. C. *J. Biol. Chem.* 260 (1985) 8838. Conradt, H. S., Buensch, A., Brossmer, R. *FEBS Lett.* 170 (1984) 295. Neu5Ac derivatives also are useful as enzyme inhibitors. Thiem, J., Treder, W. *Angew. Chem., Int. Ed. Engl.* 25 (1986) 1096. Sabesan, S., Paulsen, J. C. *J. Am. Chem. Soc.* 108 (1986) 2068. For example, 2-deoxy-Neu5Ac may be an inhibitor of CMP-Neu5Ac synthetase, a key enzyme in the biosynthesis of glyconjugates.

Neu5Ac and derivatives currently are prepared from natural sources. Schauer, R. *Adv. Carbohydr. Chem. Biochem.* 40 (1982) 131. Schauer, R. "Sialic Acids," Springer-Verlag: Wien and New York, 1982. Enzymatic aldol condensations provide an efficient alternative for asymmetric C—C coupling, which is one of the most interesting and challenging problems in synthetic organic chemistry. Whitesides, G. M., Wong, C. H. *Angew. Chem. Int. Ed. Engl.* 24 (1985) 617. Wong, C. H. in "Enzymes as Catalysts in Organic Synthesis," Schneider, M. P., Ed.; Reidel; Dordrecht, Holland, 1986; pp 199–216. Bednarski, M. D., Crans, D. C., Discosimo, R., Simon, E. S., Stein, P. D., Whitesides, G. M. *Tetrahedron Lett.*, in press. Effenberger, F., Straub, A. *Tetrahedron Lett.* 28 (1987) 1641. Durrwachter, J. R., Druekhammer, D. G., Nozaki, K., Sweers, H. M., Wong, C. H. *J. Am. Chem. Soc.* 108 (1986) 7812. Masamune, S., Choy, W., Peterson, J. S., Sita, L. R. *Angew. Chem., Int. Ed. Engl.* 24 (1985) 1. Evans, D. A. *Aldrichimica Acta* 15 (1982) 23. Evans, D. A., Nelsh, J. V., Tabar, T. R. *Top. Sterochem.* 13 (1982) 1. Most of the current methods used in the aldol reaction, however, depend upon the formation of metal-enolate complexes, which are unstable in aqueous media.

Although several chemical methods are available for synthesis of Neu5Ac and derivatives, many of the methods are expensive and may require complex protection and deprotection methods. Julina, R., Muller, I., Vasella, A., Wyler, R. *Carbohydr. Res.* 164 (1987) 415. Danishefsky, S. J., DeNinno, M. P. *J. Org. Chem.* 51 (1986) 2615. Conforth, J. W., Firth, M. G., Cottscalk, A. *Biochem. J.* 68 (1958) 57.

SUMMARY OF THE INVENTION

The present invention provides a chemical method for synthesizing new 2-deoxy-Neu5Ac derivatives.

DETAILED DESCRIPTION OF THE INVENTION

Figure 1:
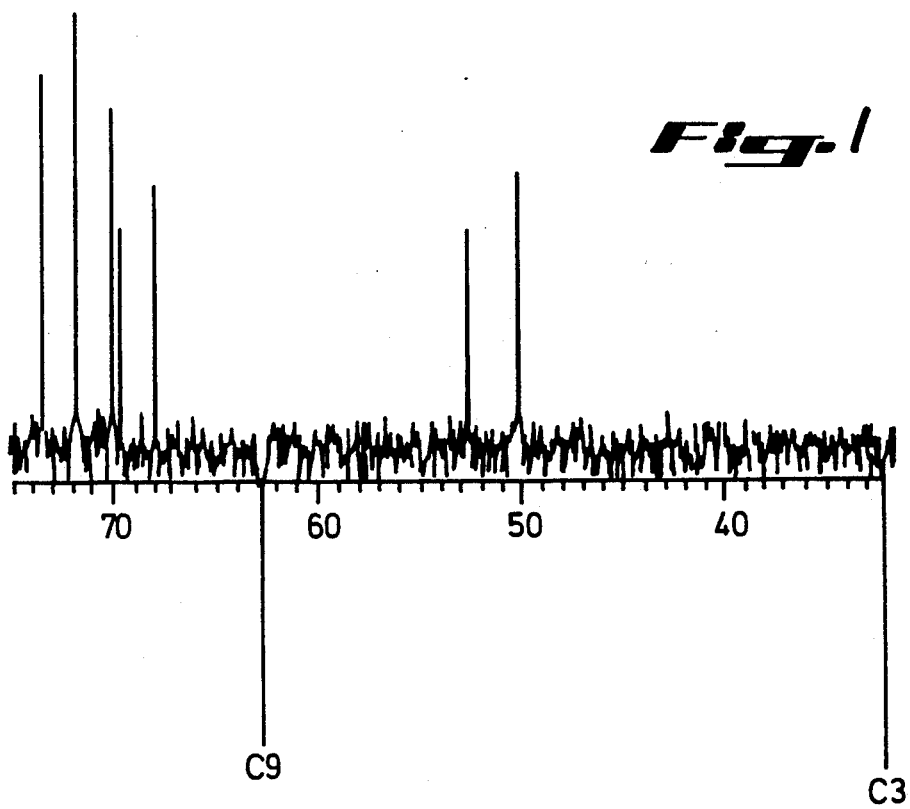
Figure 2:
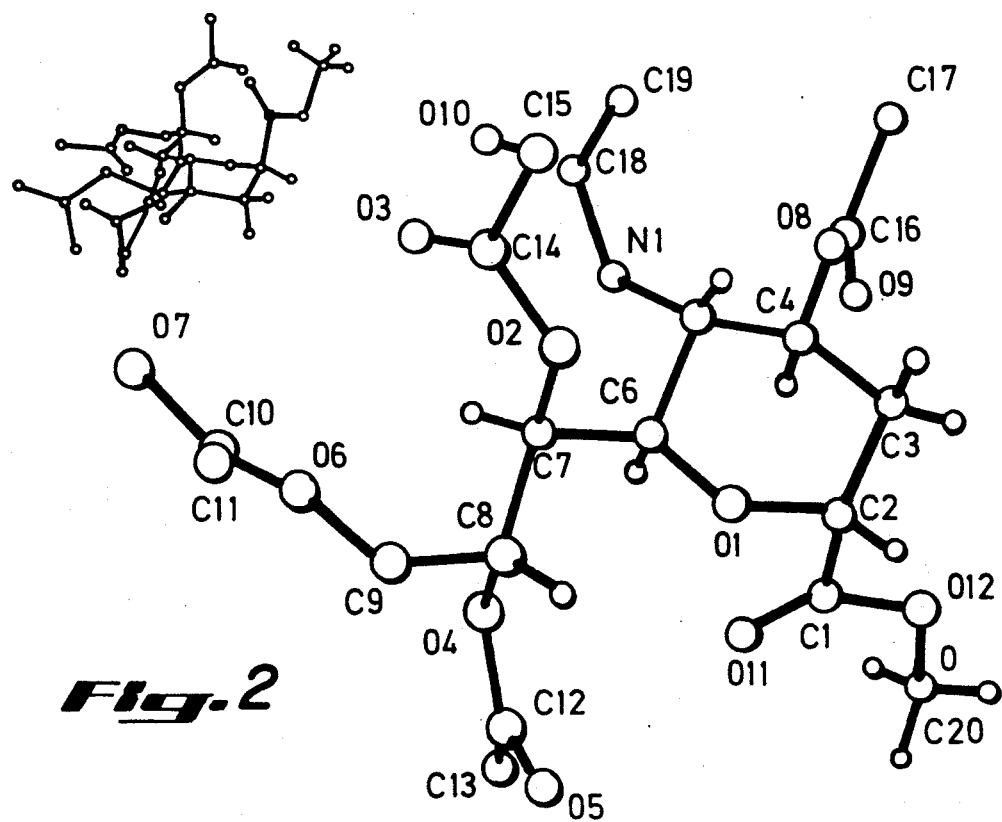

FIG. 1 represents a portion of the spectrum of 2-Deoxy-alpha-Neu-4,5,7,8,9-Ac$_5$-OMe obtained from an attached proton test; and FIG. 2 illustrates the structure of the alpha-anomer in the chair conformation.

DETAILED DESCRIPTION OF THE INVENTION

Neu5Ac aldolase is commercially available from microbial sources and is fairly inexpensive. The microbial enzyme from Toyobo costs $100 per 710 U. The Neu5Ac aldolase used in the examples (microorganisms, E.C. 4.1.3.3) was obtained from Toyobo. Industrial-scale hyperproduction of this enzyme by a gene-cloned strain of *Escherichia coli* (pNAL1) recently has been reported. Aisaka, K., Tamura, S., Arai, Y., Uwajima, T., *Biotechnol. Lett.* 9 (1987) 633. The *E. coli* enzyme is a trimer with a molecular weight of about 98,000. Uchida, Y., Tsukada, Y., Sugimori, T., *J. Biochem.* 96 (1984) 507. The equilibrium constant in the direction of formation of Neu5Ac using the Neu5Ac aldolase catalyzed reaction is 12.7 $M^{-1}$. This requires a 7-10-fold excess of pyruvate for the high conversion of the more expensive ManNAc to Neu5Ac. Uchida, Y., Tsukada, Y., Sugimori, T. *J. Biochem.* 96 (1984) 507.

L-Lactate dehydrogenase (rabbit muscle, E.C. 1.1.1.27), ManNAc, pyruvic acid sodium salt, and NADH were obtained from Sigma. Neu5Ac aldolase was immobilized as described in Pollak, A., Blumenfeld, H., Wax, M., Baugh, R. L. , Whitesides, G. M. *J. Am. Chem. Soc.* 102 (1980) 6324, incorporated herein by reference. The purity of Neu5Ac was determined using Neu5Ac aldolase, L-lactate dehydrogenase, and NADH in a coupled reaction. Tetrahydrofuran and 1,4-dioxane were distilled from sodium-benzophenone ketal, methanol was distilled from calcium hydride, and triethylamine was distilled from barium oxide using known procedures. E.g., Perrin, D. D., Armarego, W. L. F., Perrin, D. R. *Purification of Laboratory Chemicals*, Pergamon Press, NY (2d ed. 1986), incorporated herein by reference. All other solvents and chemicals were of reagent grade and were used as received.

UV absorbance changes were measured on a Beckman DU-70 spectrophotometer. $^1$H-NMR spectra were obtained on Varian XL-200 and XL-400 spectrometors at 200 and 400 MHz, respectively. $^{13}$C-NMR spectra were obtained on Varian XL-200 and XL-400 spectrometers operating at 50 and 100 MHz, respectively. Low-resolution mass spectra were obtained on a Hewlett-Packard 5995C quadrupole gas chromatograph-mass spectrometer operating at 70 eV. High-resolution mass spectra were obtained on a VG Analytical 70S high-resolution double-focusing magnetic sector mass spectrometer also operating at 70 eV. Nicolet R3m/V X-ray diffractometer and SHELXTL (version 5) software were used in the single-crystal X-ray structure determinations. Melting points were determined on a Fischer-Johns capillary melting point apparatus. Thinlayer chromatography was done on 0.25 mm layers of silica gel (60 A) on glass-backed plates supplied by J. T. Baker Co., and the compounds were visualized by spraying the plates with a 10% sulfuric acid in ethanol solution and heating. Silica gel column chromatography was done with Baker flash chromatography silica gel (230–400 mesh).

Preparation of Neu5Ac. Two reactions for the synthesis of Neu5Ac were carried out with ManNAc and pyruvate as the substrates and insoluble PAN-immobilized Neu5Ac aldolase as the catalyst on 30–40 mmol scales.

(a) In a 500 mL, three-necked flask equipped with a magnetic stirring bar were placed 6.64 g (30 mmol) of N-acetyl-D-mannosamine (ManNAc), 24.1 g (210 mmol) of sodium pyruvate (the excess of pyruvate is required to drive the reaction toward product formation and maximize consumption of the more expensive ManNAc), 0.1 g of sodium azide, 140 mL of distilled water, and 10 mL of 0.1 M phosphate buffer (pH 7.5). The solution was adjusted to pH 7.5 with 1 N NaOH, and the volume of the solution was increased to 180 mL by the addition of distilled water. The reaction was initiated by the addition of 40 mL of enzyme gel suspension (30U). The total volume of solution was 220 mL. The solution was stirred at room temperature, and the reaction was monitored by $^1$H-NMR spectroscopy. Periodically, a small aliquot (200 μL) was withdrawn and the enzyme-containing gels were removed by centrifugation. The mother liquor was freeze-dried, and the solids were dissolved in $D_2O$ containing DSS. A $^1$H-NMR spectrum of this solution was recorded. The ratio of ManNAc to Neu5Ac was calculated based on the integrals of the peaks from the N-acetyl groups of both compounds (2.06 ppm for Neu5Ac, 2.10 ppm for ManNAc) and from the $C_2$-methylene group of Neu5Ac. The reaction was stopped when the conversion of ManNAc to Neu5Ac reached 87% (4 days). The enzyme-containing gels were recovered by centrifugation and washed twice with distilled water. The recovery of the enzyme was 97%. The combined mother liquor was subjected to Bio-Rad AG 1-X8 (formate form, 100–200 mesh) column chromatography as described in Schauer, R. *Methods Enzymol.* 50C (1978) 64, to yield 6.21 g (20.1 mmol, 67%). The $^1$H-NMR spectrum of the product in $D_2O$ was identical to that of authentic Neu5Ac and found to be 96% pure by enzymatic assay.

(b) The second reaction was run with the recovered enzyme under the same conditions with exceptions in the amounts of substrates (40 mmol of ManNAc and 400 mmol of pyruvate) and the volume of solution (260 mL). The 10-day operation gave 91% conversion of ManNAc to Neu5Ac. The recovered enzyme retained 50% of its initial activity, and the products in solution were stored at −10° C. until further purified. The excess pyruvate was removed three step procedure. Fifty-two mL portions of the solution were passed through a 2.5×40 cm column of Dowex 50W-X8 (hydrogen form) with water elution. The portion of the eluent which contained the product was lyophilized to a paste. The paste was slurried in ethyl acetate and the Neu5Ac product recovered by filtration. The collected white powder was dried under a stream of dry air to yield 2.7 g of Neu5Ac as a mono-hydrate. The $^1$H-NMR spectrum of the product so obtained was identical to the reported spectrum. Brown, E. B., Brey, W. S.,Jr., Weltner, W.,Jr. *Biochem. Biophys. Acta* 399 (1975) 124–30.

The synthesis of Neu5Ac was advantageous for several reasons. First, the high conversion of the more expensive ManNAc to Neu5Ac was achieved by using a 7-10-fold excess of pyruvate. The excess of pyruvate could be removed easily and did not make the isolation of products complicated. Second, the synthesis used highly stable and fairly inexpensive microbial enzymes in the PAN-immobilized form. Thus, it should be possible to prepare large quantities (>50 g) of products by repeating the use of the enzyme several times. Third, though expensive commercial ManNAc was used as a starting material, ManNAc can be prepared readily by the base-catalyzed isomerization of N-acetyl-D-glucosamine (GluNAc). Conforth, J. W., Firth, M. G., Cottscalk, A. *Biochem. J.* 68 (1958) 57. The GluNAc epimerase-catalyzed isomerization (when the enzyme is readily available) coupled with the NeuNAc aldolase reaction might provide a better solution for the direct synthesis of NeuNAc from inexpensive GluNAc. Ghosh, S., Roseman, S. *J. Biol. Chem.* 240 (1965) 1531. Overall, this synthesis illustrates a practical use of Neu5Ac aldolase in the synthesis of carbohydrates.

EXAMPLE Preparation of methyl 4,7,8,9,-tetra-O-acetyl-N-acetyl-2-deoxy-D-neuraminate (2-deoxy-Neu4,5,7,8,9Ac5OMe)

2-Deoxy-Neu5Ac derivatives, potential inhibitors of Neu5Ac-associated enzymes, were synthesized from Neu5Ac. The synthesis of 2-deoxy-α-Neu4,5,7,8,9Ac5OMe (5) is shown below in Scheme I. The synthesis of the β-anomer (6) is shown in Scheme II.

Scheme I

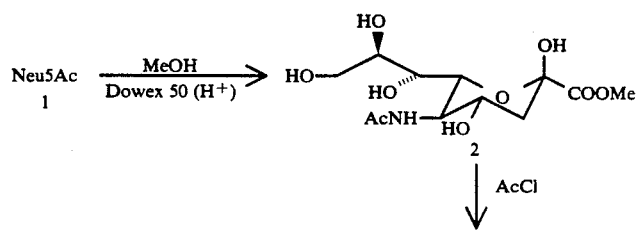

-continued

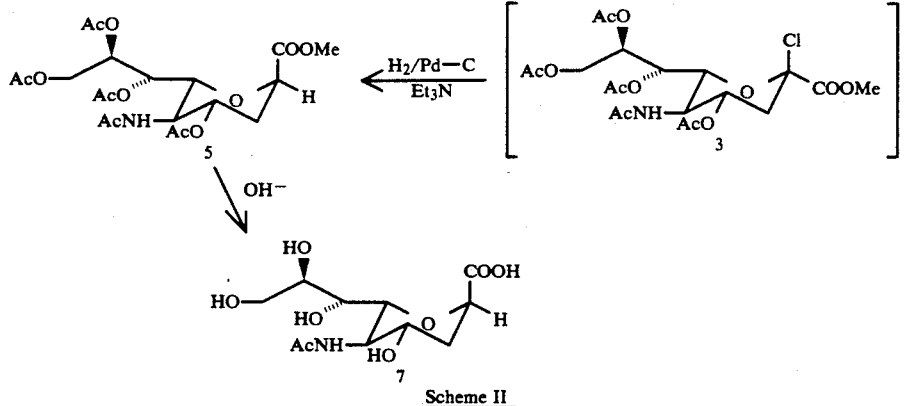

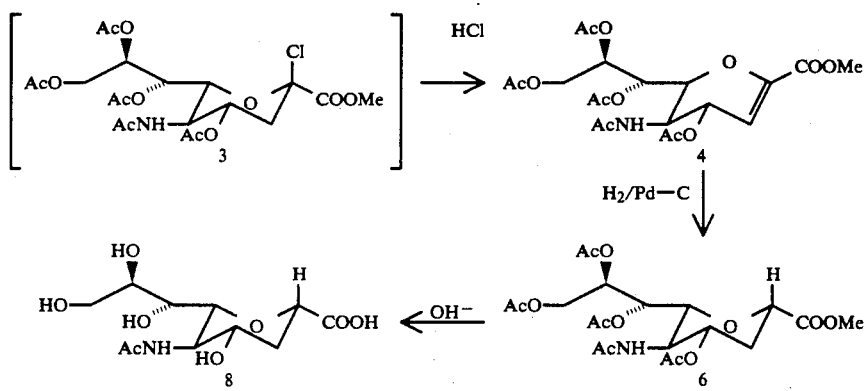

Scheme II (a) Preparation of the α-Anomer (5 of Scheme I)

A sample of methyl 4,7,8,9-tetra-O-acetyl-N-acetyl-2-chloro-β-neuraminate (3) was prepared from 200 mg of Neu5Ac by (a) esterfication of the acid function in methanol containing dried Dowex 50 ($H^{30}$) resin, as described in Kuhn, R., Lutz, P., MacDonald, D. L. Chem. Br. 99 (1966) 611, incorporated herein by reference, followed by (b) simultaneous acetylation and chlorination of the crude ester by acetyl chloride (5.5 mL, 26° C.), as described in Ogura, H., Furuhata, K., Itoh, M., Shitori, Y. Carbohydr. Res 158 (1986) 37, incorporated herein by reference. Protection of the hydroxyl group also could be accomplished using other standard procedures and/or using other protecting groups, such as described in Greene, T. W. Protective Groups in Organic Synthesis. John Wiley & Sons (1981) Ch2:(protection of OH groups):Ch5(protection of COOH groups); Haines, A. H. Advances in Carbohydrate Chem. and Biochem. 33 (1976) 101–109. After 12 h the volatile components were removed in vacuo, and the residue was azeotroped twice with 8 mL portions of tetrahydrofuran. The residue (320 mg, ca. 100%) was dissolved in 4.5 mL of 1,4-dioxane, and 0.28 mL (3 equiv) of triethylamine was added. The solution was transferred to a Parr hydrogenation bottle with the help of an additional 11.5 mL of 1,4-dioxane. The solution was hydrogenated over 200 mg of 10% palladium-on-carbon under 40 psi of hydrogen gas on a low-pressure Parr hydrogenation apparatus. After 20 h, the excess hydrogen gas was released, the solution filtered, and the catalyst washed with 30 mL of 1,4-dioxane. The combined filtrate and washings were evaporated in vacuo. The residue was taken up in 20 mL of ethyl acetate, washed twice with 10 mL portions of 10% potassium hydrogen sulfate and once with water, and dried over anhydrous sodium sulfate. The solution was filtered and evaporated in vacuo. The residue was dissolved in chloroform and loaded onto an 11 mm × 540 mm silica gel column, which was packed in chloroform. The product was eluted from the column with a 0–2% gradient of methanol in chloroform. The fractions containing the first product were pooled and evaporated to yield 155 mg (50%) of 2-deoxy-α-Neu4,5,7,8,9Ac5OMe.

A sample of 2-deoxy-α-Neu4,5,7,8,9,Ac5OMe was dissolved in dichloromethane and two volumes of hexanes were carefully placed on top of the dichloromethane layer. The loosely covered biphasic mixture was allow to stand undisturbed at room temperature. As the solutions diffused and evaporated, large prisms were deposited from which suitable crystals were selected for X-ray crystallographic analysis: mp 146°–147° C.; $^1$H-NMR (CDCl$_3$) δ 1.87 (s, 3 H, N-Ac), 2.01, 2.02, 2.10, 2.11 (4 s, 12 H, OAc), 2.09 (ddd, 1 H, H3a, $J_{2,3a}$=6.7 Hz, $J_{3a,3e}$=13.3 Hz, $J_{3a,4}$=11.8 Hz), 2.38 (ddd, 1 H, H3e, $J_{2,3e}$=1.3 Hz, $J_{3a,3e}$=13.3 Hz, $J_{3e,4}$=4.7 Hz), 3.73 (s, 3 H, OCH$_3$), 4.03 (ddd, 1 H, H5, $J_{4,5}$=$J_{5,6}$=$J_{5,NH}$=10.2 Hz), 4.09 (dd, 1 H, H9,$J_{8,9}$=4.2 Hz, $J_{9,9'}$=12.3 Hz), 4.21 (dd 1 H, H6, $J_{5,6}$=10.6 Hz, $J_{6,7}$=1.4 Hz), 4.32 (dd, 1 H, H9', $J_{8,9'}$=2.4 Hz, $J_{9,9'}$=12.3 Hz), 4.59 (dd, 1 H, H2, $J_{2,3a}$6.7 Hz, $J_{2,3e}$=1.3 Hz), 4.87 (ddd, 1 H, H4, $J_{3a,4}$=11.8 Hz, $J_{3e,4}$=4.7 Hz, $J_{4,5}$=10.2 Hz), 5.18 (d, 1 H, NH, $J_{5,NH}$=10.2 Hz), 5.31–5.34 (m, 2 H, H7, H8); $^{13}$C-NMR (CDCl$_3$) δ 20.79 (2 C) 20.92, 21.09, 23.18, 32.00, 49.80, 52.32, 62.31, 67.62, 69.25, 69.69, 71.49, 73.12, 170.02, 170.18 (2 C), 170.73, 170.81, 171.13; MS (low-resolution) m/e 476 (M+1,2.4%), 475 (M. 0.5%), 446 (4.9%), 432 (6.4%), 416 (8.5%), 373 (25.9%), 356

(38.7%), 314 (15.0%) 295 (94.0%), 253 (100%). MS (high resolution; m/e) for $C_{20}H_{30}NO_{20}$ (M+1) calcd 476.17680, obsd 476.17625. MS (high resolution: m/e) for $C_{20}H_{29}NO_{12}$ (M) calcd 475.16898, obsd 475.16496. Proton NMR assignments listed above were confirmed by a proton DQCOSY experiment. The proton absorption at 4.59 ppm was shown to be coupled only to H3a and H3e, thus confirming its identity as the H2 proton. The observed coupling constants for the H2 proton in 2-deoxy-α-Neu4,5,7,8,9Ac5OMe were 6.7 and 1.3 Hz, respectively. A small portion of a Γ component 6 also was obtained.

FIG. 1 contains a portion of the spectrum of 2-deoxy-α-Neu4,5,7,8,9Ac5OMe obtained from an attached proton test (APT) run at 50 MHz as outlined in Ranbenstein, D. L., Nakashima, T. T., *Anal. Chem.* 51 (1979) 14651A. Patt, S. L., Shoolery, J. N., *J. Magn. Reson.* 46 (1982) 535. The inverted peaks in this spectrum correspond to the methylene and quaternary carbon absorptions; the upright peaks correspond to the methine absorptions. As expected, the absorption corresponding to the quaternary carbon in the starting material is absent, and an additional methine carbon absorption is observed. The structure of the α anomer in a chair conformation (FIG. 2) was confirmed by single-crystal X-ray crystallography.

The α-anomer of the free sugar N-acetyl-2-deoxy-D-neuraminate was obtained by alkaline hydrolysis of the acetylated ester.

(b) Preparation of the β-Anomer (6 of Scheme II)

A 300 mg sample of the chloride (3), prepared as previously referenced from 200 mg of Neu5Ac, was dissolved in 40 mL of toluene. After the solvent was distilled to half-volume, 0.4 mL (5 eq.) of triethylamine was added to the hot solution. Heating was resumed and the reaction monitored by TLC (silica gel v.s 2% ethanol in ethyl acetate) until complete consumption of the chloride (3) was observed (20-30 min). The solution was evaporated in vacuo and the residue was chromatographed on a 21×150 mm flash column using 2% methanol in chloroform as the eluent. The product fractions were pooled and evaporated in vacuo and further azeotroped with toluene to remove any residual chloroform. Alternate methods of elimination of the activating group and a hydrogen at the 3-position could be used, such as that described in Baggett, N., Marsden, B. J. *J. Carbohydrat. Res.* 110 (1982) 11 α 18; Meindl, P., Tuppy, A. *Monatshefte Fur Chemie* 100 (1969) 1295-1306, incorporated herein by reference. The residue was dissolved in 30 mL of 7:3:1 toluene:ethyl acetate:methanol. The solution was transferred to a low pressure Parr bottle and hydrogenated over 200 mg of 10% palladium-on-carbon under 40 psi of hydrogen gas. After 20 h the excess hydrogen gas was released, the solution filtered, and the catalyst washed successively with 10 mL of ethyl acetate and 10 mL of methanol. The combined filtrate and washings were evaporated to dryness. The residue was taken up in 20 mL of ethyl acetate and washed successively with 10 mL portions of 10% aqueous potassium hydrogen sulfate, water, saturated aqueous sodium bicarbonate, and brine. After being dried over magnesium sulfate, the solution was evaporated in vacuo. The residue was dissolved in chloroform and loaded onto a 21×360 mm silica gel column. The product was eluted from the column with 600 mL of 1:1 ethyl acetate:hexane followed by 0-2% ethanol in ethyl acetate. The product fractions were pooled and evaporated to yield 150 mg (52%) of (6). The product was crystallized from methylene chloride-hexane: mp 181°-183° C.; $^1$H-NMR (CDCl$_3$) δ 1.82 (ddd, 1H, H3a, $J_{2,3a}$=12.2 Hz, $J_{3a,3e}$=12.9 Hz, $J_{3a,4}$=11.2 Hz), 1.86 (s, 3H, N-Ac), 2.01 (s, 6H, 2-OAc), 2.04 (s, 3H, OAc), 2.11 (s, 3H, OAc), 2,38 (ddd, 1H, H3e, $J_{2,3e}$=2.3 Hz, $J_{3a,3e}$=12.9 Hz, $J_{3e,4}$=4.9 Hz), 3.68 (dd, 1H, H6, $J_{5,6}$=10.4 Hz, $J_{6,7}$=2.2 Hz), 3.74 (s, 3H, OMe), 3.99 (ddd, 1H, H5, $J_{4,5}$=10.3 Hz, $J_{5,6}$=10.4 Hz, $J_{NH,5}$=10.0 Hz), 4.04 (dd, 1H, H2, $J_{2,3a}$=12.2 Hz, $J_{2,3e}$=2.3 Hz), 4.12 (dd, 1H, H9, $J_{8,9}$=7.4 Hz, $J_{9,9'}$=12.4 Hz), 4.64 (dd, 1H, H9', $J_{8,9'}$=2.5 Hz, $J_{9,9'}$=12.4 Hz), 5.01 (ddd, 1H, H4, $J_{3a,4}$=11.2 Hz, $J_{3e,4}$=4.9 Hz, $J_{4,5}$=10.3 Hz), 5.21 (ddd, 1H, H8, $J_{7,8}$=4.7 Hz, $J_{8,9}$=7.4 Hz, $J_{8,9'}$=2.5 Hz), 5.34 (dd, 1H, H7, $J_{6,7}$=2.2 Hz, $J_{7,8}$=4.7 Hz), 5.56 (d, 1H, NH, $J_{NH,5}$=10.0 Hz); $^{13}$C-NMR (CDCl$_3$) δ 20.79, 20.81, 20.89, 20.93, 23.22, 33.49, 49.67, 52.49, 62.43, 68.13, 71.34, 71.61, 74.49, 77.65, 168.99, 170.21, 170.31, 170.38, 170.57, 170.98; MS (low resolution; m/e) 475, 432, 416, 373, 356, 355, 330, 313, 300, 295, 253, 186, 101; MS (high resolution; m/e) for $C_{20}H_{30}NO_{12}$ (m+1) Calcd. 476.17680, obsd.: 476.17510. MS (high resolution; m/e) for $C_{20}H_{29}NO_{12}$ (m) Calcd. 475.16898, obsd. 475.16588. Proton NMR assignments listed above were confirmed by a proton DQCOSY experiment. The proton absorption at 4.04 ppm was shown to be coupled only to H3a and H3e thus confirming its identity as the H2 proton.

(c) Preparation of 2-deoxy-Neu5Ac

The α and β anomers of the free sugar N-acetyl-2-deoxy-D-neuraminate were obtained by alkaline hydrolysis of the corresponding acetylated esters. This is illustrated by the following procedure for the β-anomer.

A rapidly stirred suspension of 110 mg (0.23 mmol) of 2-deoxy-α-Neu4,5,7,8,9AC5OMe (6) in 10 mL of water was adjusted to pH 11.5 and maintained at pH 11.5 by addition of 0.25 N NaOH. After 1.5 h five equivalents of hydroxide had been consumed and no further drop in pH was observed. The solution was passed through a 1.0×22 cm column of Dowex 50W-X8 (H+ form) and lyophilized to yield 70 mg (ca. 100%) of 2-deoxy-β-Neu5Ac (8) as a hydroscopic white powder: $^1$H-NMR (D$_2$O) d 1.66 (ddd, 1H, H3a, $J_{2,3a}$=12.0 Hz, $J_{3a,3e}$=12.8 Hz, $J_{3a,4}$=10.8 Hz), 2.04 (s, 3H, NAc), 2.43 (ddd, 1H, H3e, $J_{2,3e}$=2.4 Hz, $J_{3a,3e}$=12.8 Hz, $J_{3e,4}$=4.4 Hz), 3.50 (dd, 1H, $J_1$=9.2 Hz, $J_2$=1.1 Hz), 3.59-3.66 (m, 2H), 3.79-3.92 (m, 4H), 4.27 (dd, 1H, H2, $J_{2,3a}$=12.0 Hz, $J_{2,3e}$=2.4 Hz); $^{13}$C-NMR (D$_2$O) δ 24.64, 38.57, 54.60, 65.73, 70.88, 72.36, 72.79, 76.16, 78.16, 78.27, 177.37, 177.44; FAB MS (m/e) 294 (M+1), 276, 185, 93.

The α-anomer (5) similarly was deprotected in quantitative yield to give 2-deoxy-α-Neu5Ac (7): $^1$H-NMR (D$_2$O) δ 1.92 (ddd, 1H, H3a, $J_{2,3a}$=6.6 Hz, $J_{3a,3e}$=13.6 Hz, $J_{3a,4}$=11.6 Hz), 2.04 (s, 3H, NAc), 2.54 (ddd, 1H, H3e, $J_{2,3e}$=1.6 Hz, $J_{3a,3e}$=13.6 Hz, $J_{3e,4}$=4.8 Hz), 3.53 (dd, 1H, $J_1$=9.2 Hz, $J_2$=1.2 Hz), 3.59-3.66 (m, 1H), 3.70-3.78 (m, 1H), 3.78-3.87 (m, 4H), 4.71 (dd, 1H, H2, $J_{2,3a}$=6.6 Hz, $J_{2,3e}$=1.6 Hz).

The larger H2 coupling constants found in compounds 6 and 8, with respect to compounds 5 and 7, confirm the β-anomer identity of the former derivatives.

Each of the following reactions were attempted but failed to produce either isomer 5 or 6 of 2-deoxy-Neu4,5,7,8,9Ac5OMe. Although these reagents commonly have been used in deoxygenation of sugars, they did not work in this case: Robins, M. J., Wilson J. S., Hansske, F. *J. Am. Chem. Soc.* 105 (1983) 4059, Ogilvie, K. K., Hakimelahi, G. H., Proba, Z. A., Usman, N. *Tetrahedron Lett.* 24 (1983) 865. Lewis, M. D., Cha, J. K., Kishi, Y. *J. Am. Chem. Soc.* 104 (1982) 4976. Motherwell, W. B. *Pure Appl. Chem.* 53 (1981) 15. Barton, D. H. R., Basu, N. K., Hesse, R. H., Morehouse, F. S., Pechet, M. M. *J. Am. Chem. Soc.* 88 1966 3016.

The foregoing description has been for purposes of illustration only. Those skilled in the art will appreciate a number of variations and modifications therefrom. The following claims are intended to cover all modifications and variations within the true spirit and scope of the present invention.

What is claimed is:

1. A method for preparing the alpha-anomer of a 2-deoxy-N-acetyl-neuraminic acid ester derivative comprising:
    esterifying the acid group of N-acetyl-neuraminic acid to result in an N-acetyl neuraminic acid ester;
    protecting the hydroxyl groups of said N-acetyl-neuraminic acid ester;
    activating said protected N-acetyl-neuraminic acid ester at the 2-position without having separated the protected N-acetyl-neuraminic acid ester;
    hydrogenating said protected N-acetyl-neuraminic acid ester; and
    recovering a 2-deoxy-N-acetyl-neuraminic acid ester derivative.

2. The method of claim 1 wherein said protecting step comprises acylation of the hydroxyl groups of said N-acetyl-neuraminic acid ester.

3. The method of claim 1 wherein said activating step comprises chlorinating said protected N-acetyl-neuraminic acid ester at the 2-position.

4. The method of claim 2 wherein said activating step comprises chlorinating said protected N-acetyl-neuraminic acid ester at the 2-position.

5. The method of claim 1 further comprising the step of hydrolysing said protected N-acetyl neuraminic acid ester derivative to obtain 2-deoxy-N-acetyl-neuraminic acid.

6. The method of claim 2 further comprising the step of hydrolysing said N-acetyl neuraminic acid ester derivative to obtain 2-deoxy-N-acetyl-neuraminic acid.

7. The method of claim 3 further comprising the step of hydrolysing said N-acetyl neuraminic acid ester derivative to obtain 2-deoxy-N-acetyl-neuraminic acid.

8. The method of claim 4 further comprising the step of hydrolysing said N-acetyl neuraminic acid ester derivative to obtain 2-deoxy-N-acetyl-neuraminic acid.

9. The method of claim 1 wherein said esterification of N-acetyl-neuraminic acid comprises incubating said acid with a substantially polar alcohol in the presence of an acid catalyst.

10. The method of claim 2 wherein said esterification of N-acetyl-neuraminic acid comprises incubating said acid with a substantially polar alcohol in the presence of an acid catalyst.

11. The method of claim 3 wherein said esterification of N-acetyl-neuraminic acid comprises incubating said acid with a substantially polar alcohol in the presence of an acid catalyst.

12. The method of claim 3 wherein said protecting and activating steps of said N-acetyl neuraminic acid ester comprises a single step of incubating with acetyl chloride.

* * * * *

UNITED STATES PATENT AND TRADEMARK OFFICE
CERTIFICATE OF CORRECTION

PATENT NO. : 5,239,091
DATED : August 24, 1993
INVENTOR(S) : Wong, et al.

It is certified that error appears in the above-indentified patent and that said Letters Patent is hereby corrected as shown below:

Column 1, line 5, reading "07/711,599," should read -- 07/711,559, --.

Column 5, line 20, the middle part of the structure reading $$\xrightarrow{HCl}$$ should read $$\xrightarrow{HCl}$$

Column 5, line 39, reading "($H^{30}$)" should read -- ($H^+$) --.

Column 6, line 49, reading "allow to stand" should read -- allowed to stand --.

Column 6, line 59, reading "4.32 (dd, 1H," should read -- 4.31 (dd, 1H, --.

Column 7, line 2, reading "$C_{20}H_{30}NO_{20}$" should read -- $C_{20}H_{30}NO_{12}$ --.

Column 7, line 11, reading "a Γ component" should read -- a β component --.

Column 7, line 47, reading "11α18;" should read -- 11-18; --.

UNITED STATES PATENT AND TRADEMARK OFFICE
CERTIFICATE OF CORRECTION

PATENT NO. : 5,239,091

DATED : August 24, 1993

INVENTOR(S) : Wong, et al.

It is certified that error appears in the above-identified patent and that said Letters Patent is hereby corrected as shown below:

Column 7, line 48, reading "Fur Chemie" should read -- Für Chemie --.

Column 8, line 5, reading "2,38" should read -- 2.38 --.

Signed and Sealed this

Third Day of January, 1995

Attest:

BRUCE LEHMAN

Attesting Officer

Commissioner of Patents and Trademarks